(12) United States Patent
Forrest

(10) Patent No.: US 7,665,177 B2
(45) Date of Patent: Feb. 23, 2010

(54) CLEANING SWAB, INTEGRATED HANDLE SYSTEM AND METHOD OF MAKING SAME

(75) Inventor: Edward J. Forrest, Marietta, GA (US)

(73) Assignee: Illnois Tool Works, Inc., Glenview, IL (US)

( * ) Notice: Subject to any disclaimer, the term of this patent is extended or adjusted under 35 U.S.C. 154(b) by 808 days.

(21) Appl. No.: 11/161,865

(22) Filed: Aug. 19, 2005

(65) Prior Publication Data

US 2007/0039114 A1 Feb. 22, 2007

(51) Int. Cl.
*A47L 25/00* (2006.01)

(52) U.S. Cl. ............ 15/209.1; 15/210.1; 15/244.1

(58) Field of Classification Search .......... 15/104.94, 15/209.1, 210.1, 118, 223, 225, 244.1; 300/21; 433/216

See application file for complete search history.

(56) References Cited

U.S. PATENT DOCUMENTS

| | | | |
|---|---|---|---|
| 1,589,339 A | | 6/1926 | Goldman |
| 3,591,885 A | | 7/1971 | Fritzen, Jr. |
| 3,712,296 A | | 1/1973 | Gradone |
| 3,724,018 A | | 4/1973 | Sills |
| 4,283,809 A | * | 8/1981 | Prost ............... 15/145 |
| 4,401,130 A | | 8/1983 | Halford et al. |
| 4,767,398 A | | 8/1988 | Blasius, Jr. |
| 4,795,421 A | | 1/1989 | Blasius, Jr. et al. |
| 5,084,005 A | | 1/1992 | Kachigian |
| 5,214,821 A | | 6/1993 | Burrow et al. |
| 5,346,287 A | | 9/1994 | Burrow et al. |
| 5,460,655 A | | 10/1995 | Pisacane et al. |
| 5,511,654 A | | 4/1996 | de la Rocha |
| D370,127 S | * | 5/1996 | Bonaddio et al. ........ D5/58 |
| 5,715,559 A | | 2/1998 | Mitri |
| 5,762,494 A | | 6/1998 | Archambault |

(Continued)

FOREIGN PATENT DOCUMENTS

DE 3146080 6/1983

(Continued)

OTHER PUBLICATIONS

EP Search Report (dated Dec. 28, 2007) for EP 06118556.7 filed Aug. 7, 2006.

*Primary Examiner*—Shay L Karls
(74) *Attorney, Agent, or Firm*—Levenfeld Pearlstein, LLC

(57) ABSTRACT

A cleaning swab has an elongated handle defining a longitudinal axis and having a diameter. The handle has a cleaning head end. A cleaning head is formed from a sheet of non-linting material having a predetermined thickness so as to form a predetermined cleaning head diameter. The material forms a seal-less tip and a pair of longitudinal side seals extending along longitudinal sides of the cleaning head. Excess material forms a cleaning surface suitable for standard polish and angle physical connector polished end faces. A sleeve has a central opening for receiving the handle such that the cleaning head extends beyond an open end of the sleeve. Use of a first predetermined thickness of material forms a first swab having a cleaning head having a first diameter cleaning head and use of a second different predetermined thickness of material forms a second swab having a second different diameter. The sleeve is configured to interchangeably receive the first swab and the second swab.

13 Claims, 2 Drawing Sheets

U.S. PATENT DOCUMENTS

| | | |
|---|---|---|
| 5,855,214 A | 1/1999 | Heneghan |
| 5,947,986 A | 9/1999 | Lewis |
| 5,991,960 A * | 11/1999 | Johnson ..................... 15/210.1 |
| 6,277,090 B1 | 8/2001 | Crawford, Jr. |
| 6,393,651 B1 | 5/2002 | Forrest, Jr. et al. |
| 6,494,975 B1 * | 12/2002 | Scrymgeour et al. .......... 156/64 |
| 6,523,908 B2 | 2/2003 | Forrest, Jr. et al. |
| 2002/0088073 A1 * | 7/2002 | Kammerer et al. ......... 15/209.1 |
| 2003/0108846 A1 * | 6/2003 | Hoertsch ................... 433/216 |

FOREIGN PATENT DOCUMENTS

| | | |
|---|---|---|
| GB | 2075337 | 11/1981 |
| GB | 2349070 | 10/2000 |
| WO | WO 85/05296 | 5/1985 |

* cited by examiner

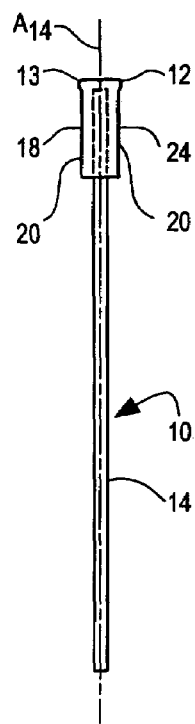
Fig. 1
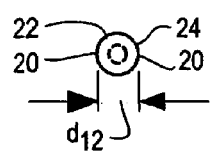
Fig. 1A
Fig. 2
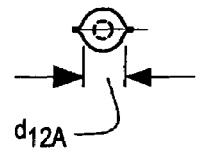
Fig. 2A
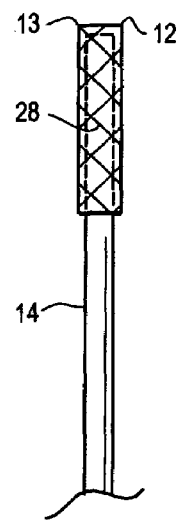
Fig. 3
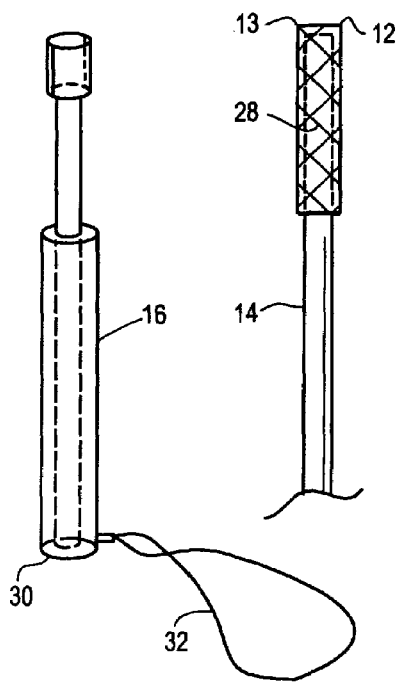
Fig. 4
Fig. 5
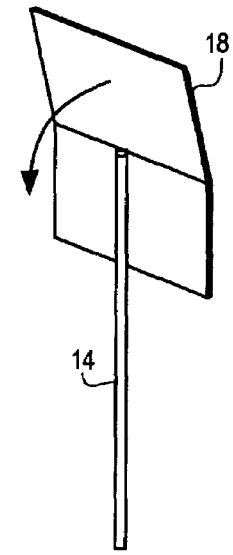
Fig. 6
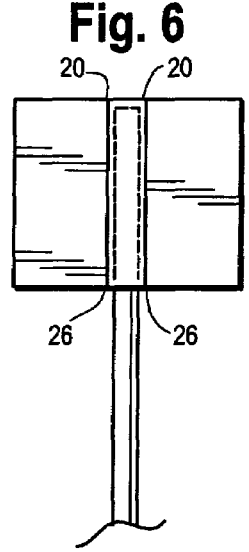

CLEANING SWAB, INTEGRATED HANDLE SYSTEM AND METHOD OF MAKING SAME

BACKGROUND OF THE INVENTION

This invention pertains to a swab for cleaning. More particularly, the present invention pertains to a swab having a cleaning portion formed from a wrapped foam and a method for making swabs.

Swabs are used in all manners of cleaning. They range from common cotton tipped swabs that are used for person hygiene and care to use in numerous areas of technology and manufacture. Because of the compact and effective nature of these swabs, they have been adopted for use in such areas as the manufacture, testing, installation and maintenance of electrical components and more specifically connectors for use in the telecommunications industry.

One particular type of connector used in the telecommunications industry is for use in fiber optic cables. In splicing or connecting fiber optic cable sections to one another, a connector is used. A typical connector includes a male portion and a female portion (typically having a ferrule). During the manufacture of these cable sections, it is not unusual for pieces of manufacturing debris, such as pieces of fiber or fiber coating debris to be left within the ends of the connectors. It is also not unusual for light oils, such as fingerprint and other natural skin oils to be found on the parts in the ends of the connectors. As will be recognized by those skilled in the art, this debris and the oils can significantly degrade or prevent the transmission capabilities of the cables across the connectors.

Numerous types of cleaning implements have been used, with some degrees of success, to clean these particularly susceptible areas. It has, however, been observed that cleaning implements formed from non-particulate removing materials may not be acceptable for use in these connectors. Specifically, it has been found that particulates can become lodged in and around the connectors, thus adversely effecting the quality of the telecommunications signal.

In addition, it has been observed that these connectors can vary in configuration and size from one type to another. For example, the connector female end can be formed as having a flat inner end surface, a concave surface or a convex surface. In addition, they can be sized in a range from about 1.0 mm to about 2.5 mm. Additionally, connectors may be single, duplex, or contained in assemblies of multiples ranging from about 6 to 48 fibers. To this end, it has been found that regardless of the type of cleaning implement used, debris that settles into and around corners and oils that are present in these areas of the connector devices may not be able to be adequately removed.

Accordingly, there exists a need for a swab-type cleaning device that can be used for cleaning connectors. Desirably, such a device leaves little to no residue from the device within the connector. Most desirably, such a cleaning device can be readily fabricated in a variety of size and efficiently removes particulate contaminants and light oils (e.g., fingerprint oils) and can be used to clean around alignment pins and corner surfaces within the connector to remove essentially all manufacturing, field, maintenance, central office or other debris.

BRIEF SUMMARY OF THE INVENTION

A cleaning swab includes an elongated handle defining a longitudinal axis and having a diameter and having a cleaning head end. A cleaning head is formed from a sheet of non-linting material. The sheet has a predetermined thickness so as to form a predetermined cleaning head diameter when wrapped around the handle. The material is sealed to form a seal-less tip and a pair of longitudinal side seals extending along longitudinal sides of the cleaning head. A sleeve has a central opening for receiving the handle such that the cleaning end extends beyond an open end of the sleeve.

Use of a first predetermined thickness of material forms a first swab having a cleaning head having a first diameter and use of a second different predetermined thickness of material forms a second swab having a second different diameter cleaning head. The sleeve is configured to interchangeably receive the first swab and the second swab.

Such a swab-type cleaning device is used for cleaning connectors, leaving little to no residue from the device within the connector. The swab is readily fabricated in a variety of sizes using one standard size handle and a sleeve for readily using (manipulating) the swab.

In one embodiment, the cleaning head longitudinal seals are configured to break away from the cleaning head. The cleaning head can be formed with a diamond pattern impression formed therein.

Cleaning head diameters of about 1.0 mm to about 2.5 mm are anticipated. The handle has a diameter of about 0.75 mm and the sleeve central opening has a diameter of about 0.75 mm to about 1.0 mm for a snug fit of the handle in the sleeve.

One non-linting material is a non-woven material. The non-woven material can be a closed cell foam, such as a microporous polyurethane foam.

A method for making the swab is also disclosed.

These and other features and advantages of the present invention will be apparent from the following detailed description, in conjunction with the appended claims.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein:

FIG. 1 is a front view of one embodiment (size) of swab;

FIG. 1A is a top view of the swab of FIG. 1;

FIG. 2 is a front view of a second embodiment (size of swab);

FIG. 2A is a top view of the swab of FIG. 2

FIG. 3 is a perspective view of the swab in the sleeve, the sleeve shown with a tether;

FIG. 4 is a partial view, as seen from the front of the swab, illustrating a diamond pattern formed in the swab cleaning head;

FIGS. 5 and 6 illustrate fabrication of the swab;

DETAILED DESCRIPTION OF THE INVENTION

Figure 7:
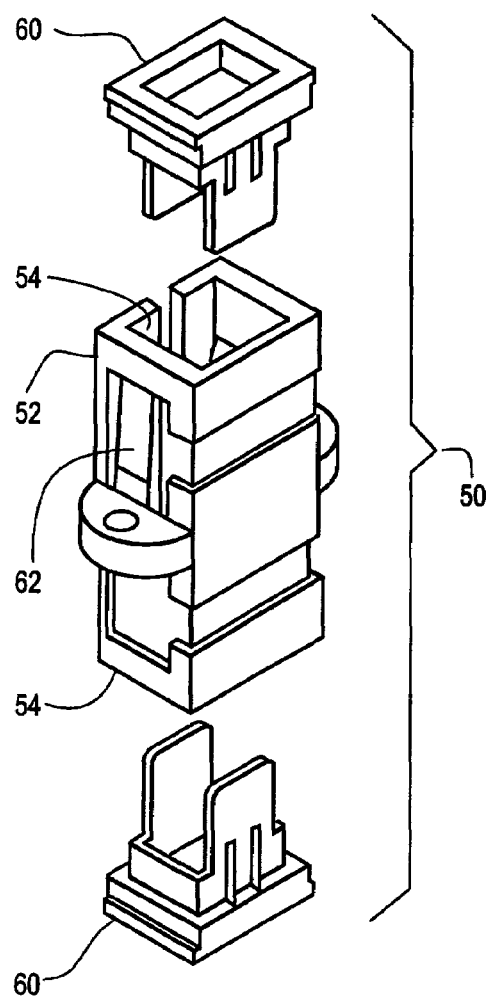
FIG. 7 is an exploded view of an exemplary connector.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description Of The Invention", relates to a requirement of the United States Patent Office, and does not imply, nor should be inferred to limit the subject matter disclosed herein.

Referring now to the figures and in particular to FIGS. 1 and 1A, there is shown a cleaning swab 10 in accordance with the principles of the present invention. The swab 10 includes, generally, a cleaning head 12 (which has excess material, as indicated at 13, to conform to both standard (flat) polish connectors and APC (angle physical polish) beveled end faces), a handle 14 to which the cleaning head 12 is mounted and a handle sleeve 16. The excess material 13 is that material "above" the tip of the handle 14 that forms a cushion-like cleaning portion. The handle 14 is elongated and has a diameter $d_{14}$ and defines a handle axis $A_{14}$.

Figure 8:
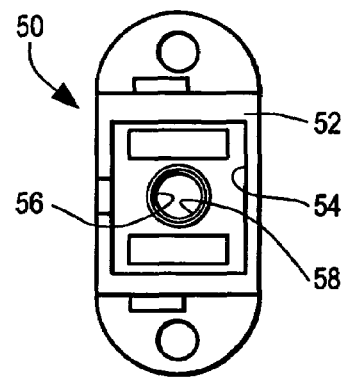
FIG. 8 is a top (or bottom) view of the connector of FIG. 7.

The swab 10 is used to clean, for example, fiber optic connector 50 components such as those illustrated in FIGS. 7 and 8. The connector 50 includes a body 52 having a pair of end cavities 54 and a central connecting passage 56 between the cavities 54. The passage 56 is formed having a sleeve 58 (that can be formed, for example from bronze or ceramic material) through which the fiber optic element F traverses. The connector 50 can include dust caps 60 to protect the cavities 54 and sleeve 58 and spring clips 62 to retain the connector 50 positioned in a panel or like housing. An exemplary connector 50 is an SC coupler commercially available from L-com of North Andover, Mass. It is anticipated that connectors 50 having sleeves 58 with different diameters, lengths and configurations may, in the future, be used. The swabs can also be used to clean test equipment "ports" such as those on EXFO OTDR and Fluke power meters.

In order to better clean the various parts of the connector 50, as well as to make the cleaning process as efficient as possible, various types of swabs are used. For example, one type of swab is a wrapped foam swab such as that disclosed in Forrest, Jr., et al., U.S. Pat. Nos. 6,393,651 and 6,523,908, both of which patents are commonly assigned with the present application and both of which are incorporated herein by reference.

While such a swab functions well under and for certain conditions, there may be instances both present and future, in which the swab may not be as configured in a most desirable configuration.

The present swab 10 includes a cleaning head 12 that is readily fabricated for use in connector sleeves 58 having different diameters or characteristics. To this end, the handle 14 of the present swab 10 is configured having one or possibly two standard diameters $d_{14}$. That is the cleaning head 12 can be fabricated with diameters $d_{12}$ from about 1.0 millimeters (mm) to more than 2.5 mm, all based on one standard handle 14 diameter $d_{14}$ (of for example, 0.75 mm).

The swab head 12 is formed from a non-linting material (indicated generally at 18) such as from a microporous foam, e.g., a polyurethane material, or other non-woven material. The material can be natural, synthetic (such as a microfiber or foam) or a combination of natural and synthetic materials. The different head diameters (see, e.g., $d_{12}$ and $d_{12a}$ in FIGS. 1, 1A and 2, 2A) are achieved using wraps of material 18 that have different basis weights which correspond to different material thicknesses. For example, using a 0.75 mm handle 14, and a 3.0 ounce (3.0 oz.) basis weight material (foam) 18, a 2.5 mm diameter $d_{12}$ swab cleaning head 12 is fabricated. Using a 2.0 oz. basis weight material (foam) 18, a 2.0 mm diameter $d_{12}$ swab cleaning head 12 is fabricated; using a 1.5 oz. basis weight material (foam) 18, a 1.25 mm diameter $d_{12}$ swab cleaning head 12 is fabricated; and using a 1.0 oz. basis weight material (foam) 18, a 1.0 mm diameter $d_{12}$ swab cleaning head 12 is fabricated.

Referring to FIGS. 5-6, the cleaning head 12 is fabricated by wrapping the material 18 around the end of the handle 14 and forming a plurality of seals (indicated at 20) in the material 18. The end or tip 22 of the cleaning head 12 is free of seals or seams so that the entire tip 22 can be used to access corners and other difficult to reach areas. In addition, the no-seal tip 22 precludes scratching of the optical fiber and/or connectors.

The head 12 is formed with first and second longitudinal seam or seal lines 20 (see FIGS. 1, 3 and 6) that are configured to break-away as desired. That is, the seals 20 are formed along two longitudinal lines extending along the cylindrical side 24 of the head 12. The longitudinal seals also include a frangible region at a juncture with the cleaning head for breaking away excess material at the side seal. In another embodiment, the excess material 26 beyond the seams (or seals) 20 can be retained on the head 12 and can be used to further assist in cleaning the connector 50.

In addition to the side seams or seals 20, the cleaning head 12 is formed having a cross-hatched or diamond pattern seam configuration (indicated at 28) extending around the head 12. The seam pattern 28 can be embossed into the head material 18. The diamond pattern 28 is preferably formed as an integral part of the manufacturing process and secures the head 12 to the handle 14 to prevent separation of the head 12 from the handle 14. In addition, the diamond pattern 28 facilitates cleaning the internal construction of the connector alignment sleeves 16 by providing regions or recesses within which debris can be collected.

Referring now to FIG. 3, to facilitate handling the swab 10, a universal handle sleeve 16 is positioned over the handle 14. A present sleeve 16 has in inside diameter $d_{16}$ of about 0.75 mm to 1.0 mm to accept or accommodate the swab handle 14. The sleeve 16 can be formed from, for example, a foam or other ergonomic and/or comfortable material that is sufficiently stiff to allow for enhanced control of the cleaning swab while at the same time sufficiently soft to allow comfortably gripping the swab 10. The sleeve 16 can include a bottom or base wall 30 to prevent over-insertion of the handle 14 in the sleeve 16. It will also be appreciated that the sleeve 16 can be fabricated from different material to achieve different objectives and can also be fabricated having different lengths to, for example, facilitate close-in work (shorter length) or work on equipment (connectors) in elevated racks or locations (longer length sleeve). The sleeve can also include a tether 32 to facilitate safekeeping of the swab 10.

Unlike known swabs, the present cleaning swab 10 is flexible in design, permitting the fabrication of different diameter swab cleaning heads 12 using a single fabrication die. In addition, the use of a standard size (diameter $d_{14}$) handle 14 reduces the inventory needed to manufacture the swabs 10, while permitting the fabrication of a wide range of swab head 12 diameters $d_{12}$. And, the use of a universal sleeve 16 provides for flexibility and enhances control and handling of the swab 10.

The seal-less or seam-less tip 22 design, along with the break-away side seals 20 and the diamond pattern seam configuration 28 facilitate cleaning otherwise hard to access areas of the connectors 50 while at the same time precluding scratching or otherwise damaging the optical fibers.

All patents referred to herein, are hereby incorporated herein by reference, whether or not specifically do so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A cleaning implement, comprising:
   a handle defining a longitudinal axis and having a diameter, the handle being elongated and having a cleaning head end;
   a cleaning head formed from a sheet of non-linting material, the cleaning head and the handle forming a cleaning swab, the sheet having a predetermined thickness so as to form a predetermined cleaning head diameter, the material being sealed to form a seal-less tip and a pair of longitudinal side seals extending along longitudinal sides of the cleaning head, the longitudinal seals having a frangible region at a juncture with the cleaning head to break-away excess material at the longitudinal seals; and
   a sleeve having a central opening for receiving the handle such that the cleaning head end of the cleaning swab extends beyond an open end of the sleeve, wherein the sleeve is configured to interchangeably receive a first cleaning swab and a second cleaning swab having a cleaning head having a different diameter than the cleaning head of the first cleaning swab.

2. The cleaning swab in accordance with claim 1 wherein the cleaning head has a diamond pattern impression formed therein.

3. The cleaning swab in accordance with claim 1 wherein the cleaning head has a diameter of about 1.0 mm to about 2.5 mm.

4. The cleaning swab in accordance with claim 1 wherein the handle has a diameter of about 0.75 mm and the sleeve central opening has a diameter of about 0.75 mm to about 1.0 mm.

5. The cleaning swab in accordance with claim 1 wherein the non-linting material is a non-woven material.

6. The cleaning swab in accordance with claim 5 wherein the non-woven material is a closed cell foam.

7. The cleaning swab in accordance with claim 6 wherein the closed cell foam is formed from a microporous polyurethane foam.

8. A method of making a cleaning implement comprising:
   providing an elongated handle having a predetermined diameter, longitudinal axis and a cleaning head end;
   providing a sheet of a non-linting, non-woven material, having a predetermined thickness;
   forming a cleaning head from the sheet of material so as to form a predetermined cleaning head diameter, the cleaning head and the elongated handle forming a cleaning swab, the material being sealed to form a seal-less tip and a pair of longitudinal side seals extending along longitudinal sides of the cleaning head, the longitudinal seals having a frangible region to break-away excess material at the longitudinal seals; and
   inserting the elongated handle of the cleaning swab into a sleeve having a central opening for receiving the handle such that the cleaning head extends beyond an open end of the sleeve, wherein the sleeve is configured to interchangeably receive a first swab and a second swab having a cleaning head having a different diameter than the cleaning head of the first swab.

9. The method in accordance with claim 8 including forming the longitudinal side seals with a frangible region at a juncture with the cleaning head for breaking away excess material at the side seal.

10. The method in accordance with claim 8 including forming a diamond pattern impression in the cleaning head.

11. The method in accordance with claim 8 wherein the sealing is by heat sealing.

12. The method in accordance with claim 8 wherein the sealing is by ultrasonic sealing.

13. The method in accordance with claim 8 including interchanging the first swab from the sleeve and inserting the second swab in the sleeve to change the diameter of the cleaning swab.

* * * * *

UNITED STATES PATENT AND TRADEMARK OFFICE
CERTIFICATE OF CORRECTION

PATENT NO.        : 7,665,177 B2                                            Page 1 of 1
APPLICATION NO. : 11/161865
DATED             : February 23, 2010
INVENTOR(S)       : Edward J. Forrest It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1059 days.

Signed and Sealed this

Seventh Day of December, 2010

David J. Kappos
*Director of the United States Patent and Trademark Office*